US007998080B2

(12) United States Patent
Ben-Ari et al.

(10) Patent No.: US 7,998,080 B2
(45) Date of Patent: Aug. 16, 2011

(54) METHOD FOR MONITORING BLOOD FLOW TO BRAIN

(75) Inventors: Shlomi Ben-Ari, Binyamina (IL); Alon Rappaport, Tel-Aviv (IL); Aharon Shapira, Moshav Givat-Chen (IL)

(73) Assignee: Orsan Medical Technologies Ltd., Natania (IL)

( * ) Notice: Subject to any disclaimer, the term of this patent is extended or adjusted under 35 U.S.C. 154(b) by 1476 days.

(21) Appl. No.: 10/893,570

(22) Filed: Jul. 15, 2004

(65) Prior Publication Data

US 2005/0054939 A1     Mar. 10, 2005

Related U.S. Application Data

(63) Continuation-in-part of application No. PCT/IL03/00042, filed on Jan. 15, 2003.

(60) Provisional application No. 60/348,278, filed on Jan. 15, 2002.

(51) Int. Cl.
*A61B 5/02*     (2006.01)

(52) U.S. Cl. .......................... 600/506; 600/504; 600/507

(58) Field of Classification Search .................. 600/506
See application file for complete search history.

(56) References Cited

U.S. PATENT DOCUMENTS

| 4,308,873 | A | 1/1982 | Maynard |
| 4,984,567 | A | 1/1991 | Kageyama et al. |
| 5,040,540 | A | 8/1991 | Sackner |
| 5,068,619 | A | 11/1991 | Nakano et al. |
| 5,265,615 | A | 11/1993 | Frank et al. |
| 5,282,840 | A | * | 2/1994 | Hudrlik ........................... 607/28 |
| 5,353,802 | A | 10/1994 | Ollmar et al. |
| 5,396,893 | A | 3/1995 | Oberg et al. |
| 5,694,939 | A | 12/1997 | Cowings |
| 5,746,214 | A | 5/1998 | Brown et al. |
| 5,749,369 | A | 5/1998 | Rabinovich et al. |
| 5,788,643 | A | 8/1998 | Feldman |
| 6,091,977 | A | 7/2000 | Tarjan et al. |
| 6,117,089 | A | 9/2000 | Sinha |
| 6,169,914 | B1 | 1/2001 | Hovland |
| 6,223,069 | B1 | 4/2001 | Pfeiffer et al. |
| 6,245,027 | B1 | 6/2001 | Alperin |
| 6,413,223 | B1 | 7/2002 | Yang et al. |
| 6,491,647 | B1 | 12/2002 | Bridger et al. |
| 6,773,407 | B2 | 8/2004 | Yost et al. |
| 6,819,950 | B2 | 11/2004 | Mills |

(Continued)

FOREIGN PATENT DOCUMENTS

DE     10061189     6/2002

(Continued)

OTHER PUBLICATIONS

Bonmassar et al. "The Spape of Electrical Impedance Spectroscopy (EIS) Is Altered in Stroke Patients", Proceedings of the 26th Annual International Conference of the IEEE EMBS, San Francisco, CA, USA, Sep. 1-5, 2005, p. 3443-3446, 2005.

(Continued)

*Primary Examiner* — Patricia C Mallari

(57) ABSTRACT

A method of estimating blood flow in the brain, comprising:
a) causing currents to flow inside the head by producing electric fields inside the head;
b) measuring at least changes in the electric fields and the currents; and
c) estimating changes in the blood volume of the head, using the measurements of the electric fields and the currents.

26 Claims, 7 Drawing Sheets

U.S. PATENT DOCUMENTS

| | | |
|---|---|---|
| 6,832,113 B2 | 12/2004 | Belalcazar |
| 6,875,176 B2 | 4/2005 | Mourad et al. |
| 6,976,963 B2 | 12/2005 | Clift |
| 6,996,428 B2 | 2/2006 | Kislov et al. |
| 7,041,063 B2 | 5/2006 | Abreu |
| 2004/0010185 A1 | 1/2004 | Kimball et al. |
| 2004/0034294 A1 | 2/2004 | Kimball et al. |
| 2004/0049105 A1 | 3/2004 | Crutchfield et al. |
| 2005/0054939 A1 | 3/2005 | Shapira et al. |
| 2006/0094964 A1 | 5/2006 | Ragauskas et al. |
| 2006/0122523 A1* | 6/2006 | Bonmassar et al. .......... 600/506 |
| 2006/0200033 A1* | 9/2006 | Keren et al. .................... 600/504 |
| 2007/0287899 A1 | 12/2007 | Poupko et al. |
| 2008/0004904 A1 | 1/2008 | Tran |
| 2008/0021332 A1 | 1/2008 | Brainard, III |
| 2008/0200787 A1 | 8/2008 | Shapira et al. |
| 2008/0275352 A1 | 11/2008 | Shapira et al. |
| 2009/0227881 A1 | 9/2009 | Reichman et al. |

FOREIGN PATENT DOCUMENTS

| | | |
|---|---|---|
| EP | 0314088 | 5/1989 |
| EP | 1057498 | 12/2000 |
| GB | 1538695 | 1/1979 |
| JP | 01-113645 | 5/1989 |
| JP | 03-118038 | 5/1991 |
| JP | 06-078888 | 3/1994 |
| JP | 2000-325324 | 11/2000 |
| JP | 2001-104274 | 4/2001 |
| JP | 2002-010986 | 1/2002 |
| JP | 2005-500116 | 1/2005 |
| RU | 2141249 | 11/1999 |
| WO | WO 96/16692 | 6/1996 |
| WO | WO 02/071923 | 9/2002 |
| WO | WO 02/087410 | 11/2002 |
| WO | WO 03/017834 | 3/2003 |
| WO | WO 03/059164 | 7/2003 |
| WO | WO 2006/006143 | 1/2006 |
| WO | WO 2006/011128 | 2/2006 |
| WO | WO 2006/0134501 | 12/2006 |
| WO | WO 2006/134501 | 12/2006 |
| WO | WO 2008/072223 | 6/2008 |
| WO | WO 2006/087696 | 8/2008 |
| WO | WO 2010/041204 | 4/2010 |
| WO | WO 2010/041205 | 4/2010 |
| WO | WO 2010/041206 | 4/2010 |

OTHER PUBLICATIONS

Grönlund et al. "High Frequency Variability of Transcephalic Electrical Impedance—A New Parameter for Monitoring of Neonatal Cerebral Circulation", IEEE, p. 2513-2515.

Moshkalenko et al. "Slow Rhythmic Oscillations With the Human Cranium: Phenomenology, Origin, and Informational Significance", Human Physiology, 27(2): 171-178, 2001. Translated From Fiziologiya Cheloveka, 27(2): 47-55, 2001.

Ragauskas et al. "Implementation of Non-Invasive Brain Physiological Monitoring Concepts", Medical Engineering & Physics, 25: 667-678, 2003.

Weindling et al. "Effect of Electrode Size on the contributions of Intracranial and Extracranial Blood Flow to the Cerebral Electrical Impedance Plethysmogram", Medical & Biological Engineering & Computing, 20: 545-549, Sep. 1982.

Czosnyka "Cerebral Perfusion in Head-Injured Patients: A Nonivasive Assessment Using Transcranial Doppler Ultrasonography", Journal of Neurosurgery, 88: 802-808, 1998.

Grönlund et al. "Transephalic Electrical Impedance Provides a Means for Quantifying Pulsatile Cerebral Blood Volume Changes Following Head-Up Tilt", Early Human Development, 47: 11-18, 1997.

Ragauskas et al. "Implement of Non-Invasive Brain Physiological Moniitoring Concepts", Medical Engineering & Physics 25: 667-678, 2003.

Traczewski et al. "The Role of Computerized Rheoencephalography in the Assessment of Normal Pressure Hydrocephalus",Journal of Neutrotrauma, 22 (7): 836-843, 2005.

Wintermark et al. "Comparatibe Overview of Brain Perfusion Imaging Techniques", Stroke, vol. 36e, p. 83-99, 2005.

Gronlund .J. et al.: "High frequency variability of trancephalic electrical impedance. A new parameter for monitoring of neonatal cerebral circulation?" Proceedings of the annual international conference of the engineering in medicine and biology society. Oct. 29, 1992. vol. 6. pp. 2513-2515.

J. H. Seipel and J. E. Floam, in J. Clinical Pharmacology 15, 144-154 (1975).

S. Braunfels, K.Meinhard, B.Zieher, K.P.Koetter, W.H.Maleck, and G.A.Petroianu, "A randomized, controlled trial of the efficacy of closed chest compressions in ambulances," Prehosp. Emerg. Care Jul.-Sep. 1997;1(3):128-131.

J. Webster, "Measurement of flow and Volume of blood", in John G. Webster (ed), Medical Instrumentation: Application and Design, (Wiley, 1997), pp. 332-371.

Translation of Office Action Dated Jun. 5, 2009 From the State Intellectual Property Office of the People's Republic of China Re.: Application No. 200680029920.X.

Translation of Office Action Dated Aug. 7, 2009 From the State Intellectual Property Office of the People's Republic of China Re.: Application No. 200580031089.7.

International Search Report and the Written Opinion Dated Apr. 20, 2010 From the International Searching Authority Re.: Application No. PCT/IB2009/054388.

International Search Report and the Written Opinion Dated Apr. 20, 2010 From the International Searching Authority Re.: Application No. PCT/IB2009/054392.

Response Dated May 5, 2010 to Rejection Decision of Feb. 12, 2010 From the State Intellectual Property Office of the People's Republic of China Re.: Application No. 200580031089.7.

Lovett Doust et al. "Aspects of the Cerebral Circulation During Non-REM Sleep in Healthy Controls and Psychiatric Patients, as Shown by Rheoencephalography", Psychophysiology, XP002572590, 12(5): 493-498, 1975. Abstract, p. 494, r-h Col., § 2—p.495, 1-h Col., § 5, p. 495, 1-h Col., § 1, p. 495, 1-h Col., § 5—r-h Col., § 1, p. 496, 1-h Col., Fig.1, Tables 1-2.

Communication Pursuant to Article 94(3) EPC Dated Apr. 3, 2009 From the European Patent Office Re.: Application No. 05750856.6.

Communication Pursuant to Article 94(3) EPC Dated Feb. 24, 2010 From the European Patent Office Re.: Application No. 07827394.3.

Communication Pursuant to Article 94(3) EPC Dated Mar. 29, 2010 From the European Patent Office Re.: Application No. 05750856.6.

Communication Relating to the Results of the Partial International Search Dated Dec. 28, 2009 From the International Searching Authority Re.: Application No. PCT/IB2009/054392.

Communication Relating to the Search of the Partial International Search Dated Dec. 29, 2009 From the International Searching Authority Re.: Application No. PCT/IB2009/054388.

International Search Report and the Written Opinion Dated Dec. 23, 2009 From the International Searching Authority Re.: Application No. PCT/IB2009/054394.

Rejection Decision Dated Feb. 12, 2010 From the State Intellectual Property Office of the People's Republic of China Re.: Application No. 200580031089.7 and Its Translation Into English.

Supplementary European Search Report Dated Jan. 28, 2010 From the European Patent Office Re.: Application No. 05752203.9.

Abboud et al. "Left-Right Asymmetry of Visual Evoked Potentials in Brain-Damaged Patients: A Mathematical Model and Experimental Results", Annals of Biomedical Engineering, XP000578781, 24(1): 75-86, Jan. 1, 1996. Abstract, Fig.1.

Barbosa-Silva et al. "Bioelectrical Impedance Analysis: Population Reference Values for Phase Angle by Age and Sex", The American Journal of Clinical Nutrition, 82: 49-52, 2005.

González et al. "A Theoretical Study on Magnetic Induction Frequency Dependence of Phase Shift in Oedema and Haematoma", Physiological Measurement, 27: 829-838, 2006.

Jacquy et al. "Cerebral Blood Flow and Quantitative Rheoencephalography", Electroencephalographyand Clinical Neurophysiology, 37: 507-511, 1974.

Jevning et al. "Evaluation of Consistency Among Different Electrical Impedance Indices of Relative Cerebral Blood Flow in Normal Resting Individuals", Journal of Biomedical Engineering, XP022444925, 11(1): 53-56, Jan. 1, 1989.

Keren et al. "Evaluation of an Noninvasive Continuous Cardiac Output Monitoring System Based on Thoracic Bioreactance", American Journal of Physiology: Heart Circulation Physiology, 293: H583-H589, 2007.

Seoane Martinez "Electrical Bioimpedance Cerebral Monitoring: Fundamental Steps Toward Clinical Applications", Thesis for the Degree of Doctor of Philosophy, Department of Signals and Systems, Division of Biomedical Engineering, Chalmers University of Technology, Göteborg, Sweden & School of Engineering, University College of Borås, Borås, Sweden, 153 P., 2007.

Steiner et al. "Continuous Monitoring of Cerebrovascular Pressure Reactivity Allows Determination of Optimal Cerebral Perfusion Pressure in Patients With Traumatic Brain Injury", Critical Care Medicine, 30(4): 733-738, Apr. 2002. Abstract.

Stiefel et al. "Reduced Mortality Rate in Patients With Severe Traumatic Brain Injury Treated With Brain Tissue Oxygen Monitoring", Journal of Neurosurgery, 103(5): 805-811, Nov. 2005.

Communication Pursuant to Article 94(3) EPC Dated Jun. 2, 2010 From the European Patent Office Re. Application No. 05752203.9.

Bellner et al. "Transcranial Doppler Sonography Pulsatility Index (PI) Reflects Intracranial Pressure (ICP)", Surgical Neurology, 62(1): 45-51, Jul. 2004.

Response Dated Jul. 18, 2010 to Communication Pursuant to Article 94(3) EPC of Feb. 24, 2010 From the European Patent Office Re.: Application No. 07827394.3.

Response Dated Jul. 19, 2010 to Communication Pursuant to Article 94(3) EPC of Mar. 29, 2010 From the European Patent Office Re.: Application No. 05750856.6.

Response Dated Jul. 26, 2010 to the Written Opinion of Dec. 23, 2009 From the International Searching Authority Re.: Application No. PCT/IB2009/054394.

Response Dated Aug. 9, 2010 to the Written Opinion of Apr. 20, 2010 From the International Searching Authority Re.: Application No. PCT/IB2009/054392.

Response Dated Jul. 29, 2010 to the Written Opinion of Apr. 29, 2010 From the International Searching Authority Re.: Application No. PCT/IB2009/054388.

Invitation to Restrict or Pay Additional Fees Dated Aug. 24, 2010 From the International Preliminary Examining Authority Re. Application No. PCT/IB2009/054388.

Letter in Response Dated Dec. 7, 2010 to Telephone Conference With Examiner of Dec. 7, 2010 From the International Bureau of WIPO Re. Application No. PCT/IB2009/054392.

Letter in Response Dated Dec. 7, 2010 to Telephone Conference With Examiner of Dec. 7, 2010 From the International Bureau of WIPO Re. Application No. PCT/IB2009/054394.

Translation of Notification of Reasons for Rejection Dated Dec. 14, 2010 From the Japanese Patent Office Re. Application No. 2007-520969.

International Preliminary Report on Patentability Dated Dec. 21, 2010 From the International Preliminary Examining Authority Re. Application No. PCT/IB2009/054392.

International Preliminary Report on Patentability Dated Dec. 27, 2010 From the International Preliminary Examining Authority Re.: Application No. PCT/IB2009/054394.

International Preliminary Report on Patentability Dated Jan. 3, 2008 From the International Bureau of WIPO Re.: Application No. PCT/IB2006/050174.

International Preliminary Report on Patentability Dated Nov. 15, 2006 From the International Preliminary Examining Authority Re.: Application No. PCT/IL2005/000631.

International Preliminary Report on Patentability Dated May 23, 2007 From the International Preliminary Examining Authority Re.: Application No. PCT/IL05/00632.

International Preliminary Report on Patentability Dated Mar. 26, 2009 From the International Preliminary Examining Authority Re.: Application No. PCT/IL2007/001421.

International Search Report Dated Dec. 5, 2005 From the International Searching Authority Re.: Application No. PCT/IL05/00632.

International Search Report Dated Oct. 14, 2003 From the International Searching Authority Re.: Application No. PCT/IL03/00042.

International Search Report Dated Oct. 20, 2005 From the International Searching Authority Re.: Application No. PCT/IL2005/000631.

International Search Report Dated May 21, 2008 From the International Searching Authority Re.: Application No. PCT/IL2007/001421.

International Search Report Dated Jun. 23, 2006 From the International Searching Authority Re.: Application No. PCT/IB2006/050174.

Office Action Dated Sep. 5, 2008 From the Patent Office of the People's Republic of China Re.: Application No. 200580031088.2 and Its Translation Into English.

Office Action Dated May 23, 2008 From the Patent Office of the People's Republic of China Re.: Application No. 100580031089.7.

Written Opinion Dated Dec. 5, 2005 From the International Searching Authority Re.: Application No. PCT/IL05/000632.

Written Opinion Dated Oct. 20, 2005 From the International Searching Authority Re.: Application No. PCT/IL2005/000631.

Written Opinion Dated May 21, 2008 From the International Searching Authority Re.: Application No. PCT/IL2007/001421.

Written Opinion Dated Jun. 23, 2006 From the International Searching Authority Re.: Application No. PCT/IB2006/050174.

Response Dated Jan. 12, 2011 to Telephone Conference With Examiner of Jan. 12, 2011 From the International Bureau of WIPO Re. Application No. PCT/IB2009/054388.

International Preliminary Report on Patentability Dated Jan. 21, 2011 From the International Preliminary Examining Authority Re. Application No. PCT/IB2009/054388.

Response Dated Oct. 3, 2010 to Communication Pursuant to Article 94(3) EPC of Jun. 2, 2010 From the European Patent Office Re. Application No. 05752203.9.

Communication Relating to the Results of the Partial International Search Dated Dec. 29, 2009 From the International Searching Authority Re.: Application No. PCT/IB2009/054388.

Invitation to Pay Additional Fees Dated Aug. 24, 2010 From the International Preliminary Examining Authority Re. Application No. PCT/IB2009/054388.

Letter in Reponse Dated Dec. 7, 2010 to Telephone Conference With Examiner of Dec. 7, 2010 From the International Bureau of WIPO Re. Application No. PCT/IB2009/054392.

Letter in Reponse Dated Dec. 7, 2010 to Telephone Conference With Examiner of Dec. 7, 2010 From the International Bureau of WIPO Re. Application No. PCT/IB2009/054394.

Response Dated Jan. 12, 2011 to Telephone Conference With Examiner of Jan. 12, 2011 From the International Bureau of WIPO Re. Application No. PCT/IB2009/054388.

Translation of Notificiation of Reasons for Rejection Dated Dec. 14, 2010 From the Japanese Patent Office Re. Application No. 2007-520969.

Braunfels et al. "A Randomized, Controlled Trial of the Efficacy of Closed Chest Compressions in Ambulances", Preshop Emrge Care, 1(3): 128-131, 1997.

Gonz?lez et al. "A Theoretical Study on Magnetic Induction Frequency Dependence of Phase Shift in Oedema and Haematoma", Physiological Measurement, 27: 829-838, 2006.

Gr?nlund et al. "High Frequency Variability of Trancephalic Electrical Impedance. A New Parameter for Monitoring of Neonatal Cerebral Circulation?", Proceedings of the Annual International Conference of the Engineering in Medicine and Biology Society, 6(Conf. 14): 2513-2515, 1992. p. 2513, r-h Col., Lines 6-20.

Gr?nlund et al. "Transephalic Electrical Impedance Provides a Means for Quantifying Pulsatile Cerebral Blood Volume Changes Following Head-Up Tilt", Early Human Development, 47: 11-18, 1997.

Seipel et al. "Rheoencephalographic and Other Studies of Betahistine in Humans: I. The Cerebral and Peripheral Circulatory Effects of Single Doses in Normal Subjects", The Journal of Clinical Pharmacology, 15: 144-154, 1975.

Seoane Martinez "Electrical Bioimpedance Cerebral Monitoring: Fundamental Steps Toward Clinical Applications", Thesis for the Degree of Doctor of Philosophy, Department of Signals and Systems, Division of Biomedical Engineering, Chalmers University of Technology, G?teborg, Sweden & School of Engineering, University College of Bor?s, Bor?s, Sweden, 153 P., 2007.

Webster "Measurement of Flow and Volume of Blood", Medical Instrumentation: Appliccation and Design: 332-371, 1997.

Communication Pursuant to Article 94(3) EPC Dated Apr. 28, 2011 From the European Patent Office Re. Application No. 05752203.9.

International Preliminary Report on Patentability Dated Apr. 21, 2011 From the International Bureau of WIPO Re. Application No. PCT/IB2009/054388.

Response Dated Feb. 27, 2011 to Office Action of Aug. 12, 2010 From the State intellectual Property Office of the People's Republic of China Re. Application No. 200780051314.2.

Translation of Notification of Reasons for Rejection Dated Mar. 22, 2011 From the Japanese Patent Office Re. Application No. 2007-520968.

Official Action Dated Apr. 13, 2011 From the US Patent and Trademark Office Re. U.S. Appl. No. 11/572,141.

Communication Under Rule 71(3) EPC Dated May 18, 2011 From the European Patent Office Re.: Application No. 05750856.6.

* cited by examiner

METHOD FOR MONITORING BLOOD FLOW TO BRAIN

RELATED APPLICATION

The present application is a continuation in part of PCT Application No. PCT/IL03/00042, filed on Jan. 15, 2003. The present application also claims the benefit under §119(e) of U.S. Provisional Application No. 60/348,278, filed on Jan. 15, 2002. The disclosures of these applications are incorporated herein by reference.

FIELD OF THE INVENTION

The field of the invention is medical instrumentation, for example for measuring blood flow to the brain.

BACKGROUND OF INVENTION

There is a need to measure cerebral blood flow during several medical events and procedures, because any disturbance to the flow of blood to the brain may cause an injury to the function of the brain cells, and even death of brain cells if the disturbance is prolonged. Maintaining blood flow to the brain is especially important because brain cells are more vulnerable to a lack of oxygen than other cells, and because brain cells usually cannot regenerate following an injury. A number of common situations may cause a decrease in the general blood flow to the brain, including arrhythmia, myocardial infarction, and traumatic hemorrhagic shock. In such cases, data regarding the quantity of blood flow in the brain, and the changes in flow rate, may be vastly important in evaluating the risk of injury to the brain tissue and the efficacy of treatment. The availability of such data may enable the timely performance of various medical procedures to increase the cerebral blood flow, and prevent permanent damage to the brain.

Existing means for measuring cerebral blood flow are complex, expensive, and in some cases invasive, which limits their usefulness. Three non-portable methods that are presently used only in research are: 1) injecting radioactive xenon into the cervical carotid arteries and observing the radiation it emits as it spreads throughout the brain; 2) positron emission tomography, also based on the injection of radioactive material; and 3) magnetic resonance angiography, performed using a room-sized, expensive, magnetic resonance imaging system, and requiring several minutes to give results. A fourth method, trans-cranial Doppler (TCD) uses ultrasound and is not invasive, and gives immediate results. However, TCD fails in about 15% of patients, due to the difficulty of passing sound waves through the cranium, and it requires great skill by professionals who have undergone prolonged training and practice in performing the test and deciphering the results. Another disadvantage of TCD is that it measures only regional blood flow in the brain, and does not measure global blood flow.

Impedance measurements of the thorax are a known technique for monitoring intracellular and extracellular fluid in the lungs, in patients with congestive heart failure. This technique is effective because the resistive impedance of the thorax at low frequency depends on the volume of blood and other electrolytic fluids, which have a relatively high electrical conductivity, present outside cells. (The capacitive impedance of the thorax, on the other hand, depends largely on the volume of fluid inside cells.) A complicating effect in measuring the impedance of the thorax is the changing volume of air in the lungs during the breathing cycle, since air has a very high resistivity, and various methods have been developed to compensate for this effect. See, for example, U.S. Pat. Nos. 5,788,643, 5,749,369, and 5,746,214, the disclosures of which are incorporated herein by reference.

In these impedance measurements, current is often passed through the thorax with one set of electrodes, and a different set of electrodes is used to make voltage measurements. This "four wire" method essentially eliminates the voltage drop associated with the current flowing through any impedance in series with the thorax in the current-carrying circuit, for example due to poor contact (possibly changing unpredictably) between the current-carrying electrodes and the skin, or in the power supply producing the current. Those voltage drops, which are not of interest in measuring the impedance of the thorax, do not occur in the separate voltage-measuring circuit because it has high impedance and very little current flowing in it.

Photoplesthysmography is another technique used to monitor blood flow and blood volume, using the reflectivity of red or infrared light from the surface of the skin, for example the finger, or the earlobe. See, for example, J. Webster, "Measurement of Flow and Volume of Blood," in John G. Webster (ed.), *Medical Instrumentation: Application and Design* (Wiley, 1997).

Magnetically inducing electrical fields in the body, including the head, is used in some existing medical procedures, principally for stimulation of the peripheral or central nervous system. See, for example, PCT publication WO 96/16692, the disclosure of which is incorporated herein by reference. Peripheral nerve stimulation is also a well known unwanted side effect of the time-varying magnetic fields used in magnetic resonance imaging.

SUMMARY OF THE INVENTION

An aspect of some embodiments of the invention relates to using impedance measurements of at least part of the head to estimate blood flow to the brain. For some applications, it is not necessary to measure the absolute impedance accurately, since the blood flow is estimated, and/or the presence of significant blood flow is ascertained, by observing changes in the impedance (due to changes in blood volume) during a cardiac cycle. For some applications, even the absolute blood flow rate need not be measured accurately, but it is enough to detect changes in the blood flow rate over time. Various methods are used to make the impedance measurements more sensitive to the impedance of the brain, and less sensitive to the much greater impedance of the skull, as well as to reduce motion artifacts.

In some embodiments of the invention, the impedance of the head is measured by passing current through the head and measuring the associated voltage by electrodes. To reduce the errors in measurement that are associated with the high relative impedance of the skull, current is passed through the head using one or more pairs of current-carrying electrodes, and a separate pair of voltage-measuring electrodes, on a separate high impedance circuit, is used to measure the voltage across the head. Optionally, sensitivity to the skull impedance is further reduced by inserting the voltage measuring electrodes into the ears. Alternatively or additionally, the nose or other orifices, or thin bone areas in the skull, are used. Examples of orifices are openings in the skull, for example the eye sockets, or the foramen magnum. An example of a thin bone area is the temple.

Optionally, electrodes of large area are used, or one or more electrodes are spread out over a large area (for example, by using an annular electrode) even if the total area of the electrodes themselves is not so large, in order to focus the current to go through the interior of the head, and not so much through the scalp. Optionally, a large voltage sensing area, for example a plurality of voltage-measuring electrodes spread out over a large area and shorted together, or a single voltage-measuring electrode with a long, winding shape or with many arms spread out over a large area, is interspersed among a current-carrying electrode or electrodes similarly spread out over a large area. Optionally, when the distance between the different electrodes, or the different arms of the electrodes, is comparable to or greater than the thickness of the scalp and skull, or even just the thickness of the scalp, then the voltage measured by voltage-measuring electrode will tend to be relatively insensitive to the voltage drop across the scalp and skull, and will be relatively more sensitive to the voltage drop across the brain. For example, the individual electrodes, or the arms of the electrodes, are at least 1 mm wide, or at least 2 mm wide, or at least 5 mm wide, or at least 1 cm wide, and the electrodes are separated by similar distances. The total spread of the electrodes on each side of the head, for example, is at least 1 cm, or at least 2 cm, or at least 5 cm.

Optionally, the impedance of the head is measured over time. The change in impedance over a pulse cycle, for example, is a measure of the change in blood volume during a pulse cycle, and hence the blood flow rate. Even if there are inaccuracies in the blood flow rate measured in this way, the technique is adequate for detecting a substantial drop in blood flow to the brain that occurs during surgery, or in determining whether CPR is being performed effectively.

In some embodiments of the invention inductive measurements are used to estimate the impedance of the head, and hence the blood volume and rate of blood flow to the brain. One or more coils with alternating current flowing in them, adjacent to the head, are used to produce a changing magnetic field inside the head, and hence to induce an electric field, which drives eddy currents in the brain. The magnitude of these eddy currents depends on the impedance of the brain, and hence on the blood volume of the brain. The eddy currents in the brain are measured by the changing magnetic field, and hence voltage, which they induce in the driving coils, or in one or more separate measuring coils, which are place around the head, approximately parallel to the driving coils.

Optionally, instead of or in addition to using the driving coils or measuring coils to measure the eddy currents in the brain, voltage-measuring electrodes on the skin are used to measure the induced electric field. Alternatively or additionally, magnetic field sensors, for example Hall sensors, flux gate magnetometers, or SQUIDs, are used to measure the magnetic field. Both the induced electric field and the magnetic field depend on the impedance of the brain, because the eddy currents in the brain affect the magnetic field.

An aspect of some embodiments of the invention concerns the use of photoplethysmography to estimate the rate of blood flow to the brain, either alone or in conjunction with impedance measurements. Optionally, photoplethysmography is performed inside the ear, which makes it more sensitive to the important internal blood flow in the head, as opposed to measurements in the earlobe which depend on peripheral blood flow. A probe for photoplethysmography inside the ear is optionally combined with a voltage-measuring probe used inside the ear for impedance measurements.

There is thus provided, in accordance with an embodiment of the invention, a method of estimating blood flow in the brain, comprising:
  a) causing currents to flow inside the head by producing electric fields inside the head;
  b) measuring at least changes in the electric fields and the currents; and
  c) estimating changes in the blood volume of the head, using the measurements of the electric fields and the currents.

In an embodiment of the invention, using the measurements of electric fields and the currents comprises calculating the impedance of the head at least two different times.

In an embodiment of the invention, producing electric fields inside the head comprises placing at least two current-carrying electrodes on the head and applying at least two different voltages to the current-carrying electrodes.

Optionally, there is more than one current-carrying electrode at the same voltage.

Optionally, the current-carrying electrodes are sufficiently large in area so that a significant amount of the current flows through the interior of the skull, and not through the scalp.

Alternatively or additionally, the electrodes are spread out enough in area so that a significant amount of the current flows through the interior of the skull, and not through the scalp.

In an embodiment of the invention, measuring the electric fields comprises placing at least two voltage-measuring electrodes on the head, on a separate circuit from the current-carrying electrodes, and measuring the voltage difference between the voltage-carrying electrodes.

Optionally, placing the voltage-measuring electrodes on the head comprises placing them inside the ears.

Optionally, placing the current-carrying electrodes on the head comprises placing at least three current-carrying electrodes on the head, and applying different voltages to the current-carrying electrodes comprises applying at least three different voltages to the current-carrying electrodes so that a desired current distribution is produced in the head.

Optionally, the desired current distribution is concentrated in a desired region of the brain, and estimating the blood flow in the brain comprises estimating the blood flow in the desired region of the brain.

In an embodiment of the invention, producing electric fields inside the head comprises:
  a) placing at least one induction coil adjacent to the head; and
  b) running time-varying current through said at least one induction coils; thereby inducing the electric fields inside the head, whereby causing currents to flow inside the head comprises causing eddy currents to flow inside the head.

Optionally, the frequency distribution of the time-varying current running through the at least one induction coils is such that the eddy currents flowing in the head do not reduce the magnetic field at any point in the head by more than a factor of 3.

In an embodiment of the invention, measuring the currents inside the head comprises measuring the magnetic field produced by the eddy currents.

Optionally, measuring the magnetic field produced by the eddy currents comprises:
  a) placing two voltage-measuring electrodes on the head;
  b) measuring the induced electric field by measuring the voltage difference between the voltage-measuring electrodes; and c) subtracting the part of the electric field induced by the magnetic field produced by the currents running in the at least one induction coils, thereby finding the part of the electric field induced by the magnetic field produced by the eddy currents.

In an embodiment of the invention, the method also comprises using photoplethysmography on tissue inside the head.

Optionally, the tissue is inside the ear.

Alternatively or additionally, the tissue is inside the nose.

In an embodiment of the invention, the method is used to monitor the blood flow in a patient's brain during surgery.

Alternatively, the method is used to monitor the blood flow in a patient's brain during CPR, to verify that the CPR is being performed effectively.

Alternatively, the method is used to monitor the blood flow in the brain of a patient with a medical condition likely to lead to loss of blood flow to the brain.

There is thus also provided, in accordance with an embodiment of the invention, an apparatus for estimating blood flow to the brain, comprising:
 a) a power supply;
 b) an electric field source which uses the power supply to produce an electric field in the head, at a safe amplitude and frequency, thereby producing a current in the head;
 c) an electrical element which determines at least changes in the electric field in the head and at least changes in the current in the head, having sufficient precision to at least estimate changes in the impedance of the head; and
 d) a monitor which displays at least information telling a user when changes in the impedance of the head show a significant change in blood flow rate.

In an embodiment of the invention, the electric field source comprises at least two current-carrying electrodes, adapted for forming a good electrical connection to the head, and connected to the power supply, and the electrical element comprises:
 a) a controller in the power supply which controls one of the output voltage and the output current of the power supply, or a combination of the output voltage and output current; and
 b) a meter which measures one of voltage across the head, current through the head, or a combination of voltage across the head and current through the head which is not controlled by the controller.

Optionally, the controller in the power supply controls the output current, and the meter is a voltmeter, and there are two voltage-measuring electrodes, connected to the voltmeter, which voltage-measuring electrodes are adapted for forming a good electrical connection to the head.

Optionally, the current-carrying electrodes comprise at least three current-carrying electrodes, and at least two of the current-carrying electrodes are connected in parallel to the same voltage.

Optionally, the current-carrying electrodes are collectively sufficiently large in area so that a significant amount of the current flows through the interior of the skull, and not through the scalp.

Alternatively or additionally, the current-carrying electrodes are collectively sufficiently spread out in area so that a significant amount of the current flows through the interior of the skull, and not through the scalp.

In an embodiment of the invention, the voltage-measuring electrodes are adapted to be placed inside an opening in the head.

Optionally, the voltage-measuring electrodes are adapted to be placed inside the ears.

Optionally, the voltage-measuring electrodes are conical and padded, thereby allowing them to be pressed firmly enough into the ears to make good electrical contact, without damaging the ear drums.

Optionally, there is also a probe adapted for measuring blood flow photoplethysmographically in the ears, which probe is combined with the voltage-measuring electrodes.

In an embodiment of the invention, the at least two current-carrying electrodes comprise at least three current-carrying electrodes, and the power supply is capable of simultaneously applying at least three different voltages to the current-carrying electrodes, whereby a desired current distribution is produced inside the head.

Optionally, the current-carrying electrodes are adapted to be placed in locations on the head such that the desired current distribution is concentrated in a desired region of the brain.

In an embodiment of the invention:
 a) the power supply produces a time-varying power supply current;
 b) the means for producing an electric field in the head comprises at least one induction coil, connected to the power supply, which induces an electric field in the head by producing a time-varying magnetic field in the head, the current in the head thereby being an eddy current;
 c) the means for determining at least changes in the electric field in the head comprises a controller in the power supply, which determines the rate of change of the power supply current, and thereby determines the rate of change of the magnetic field in the head, and the induced electric field in the head; and
 d) the means for determining at least changes in the current in the head comprises a sensor which senses the magnetic field produced by the current in the head.

Optionally, the power supply is capable of operating over at least part of the range between 10 kHz and 100 kHz.

Alternatively or additionally, the power supply is capable of operating over at least part of the range between 100 kHz and 1 MHz.

Alternatively or additionally, the power supply is capable of operating over at least part of the range between 1 MHz and 10 MHz.

Alternatively or additionally, the power supply is capable of operating over at least part of the range between 10 MHz and 100 MHz.

In an embodiment of the invention, the sensor comprises at least one of the at least one induction coils.

Alternatively or additionally, the sensor comprises a separate sensing coil which measures the voltage induced by changes in magnetic flux passing through it.

Alternatively or additionally, the sensor comprises a solid-state magnetic field sensor.

Alternatively or additionally, the sensor comprises voltage-measuring electrodes which measure an electric field induced by the time-varying magnetic field produced by the at least one induction coil.

In an embodiment of the invention, there is also a photoplethysmographic blood-flow measuring probe, sized and shaped to be placed in the ears.

Optionally, the probe is sufficiently wide at its base that it cannot damage the eardrum when inserted into the ears.

Optionally, the probe is surrounded by a holding element which, when inserted into the ear, holds the probe in a position and orientation to allow repeated optical measurements of the same location.

In an embodiment of the invention, the apparatus is portable enough for use in the field by emergency medical technicians.

In an embodiment of the invention, there is also:
a) a head motion sensor; and
b) a controller which uses data from the head motion sensor to reduce motion artifacts in estimating the blood flow.

BRIEF DESCRIPTION OF THE DRAWINGS

Exemplary embodiments of the invention are described in the following sections with reference to the drawings. The drawings are generally not to scale and the same or similar reference numbers are used for the same or related features on different drawings.

DETAILED DESCRIPTION OF EXEMPLARY EMBODIMENTS

Figure 1A:
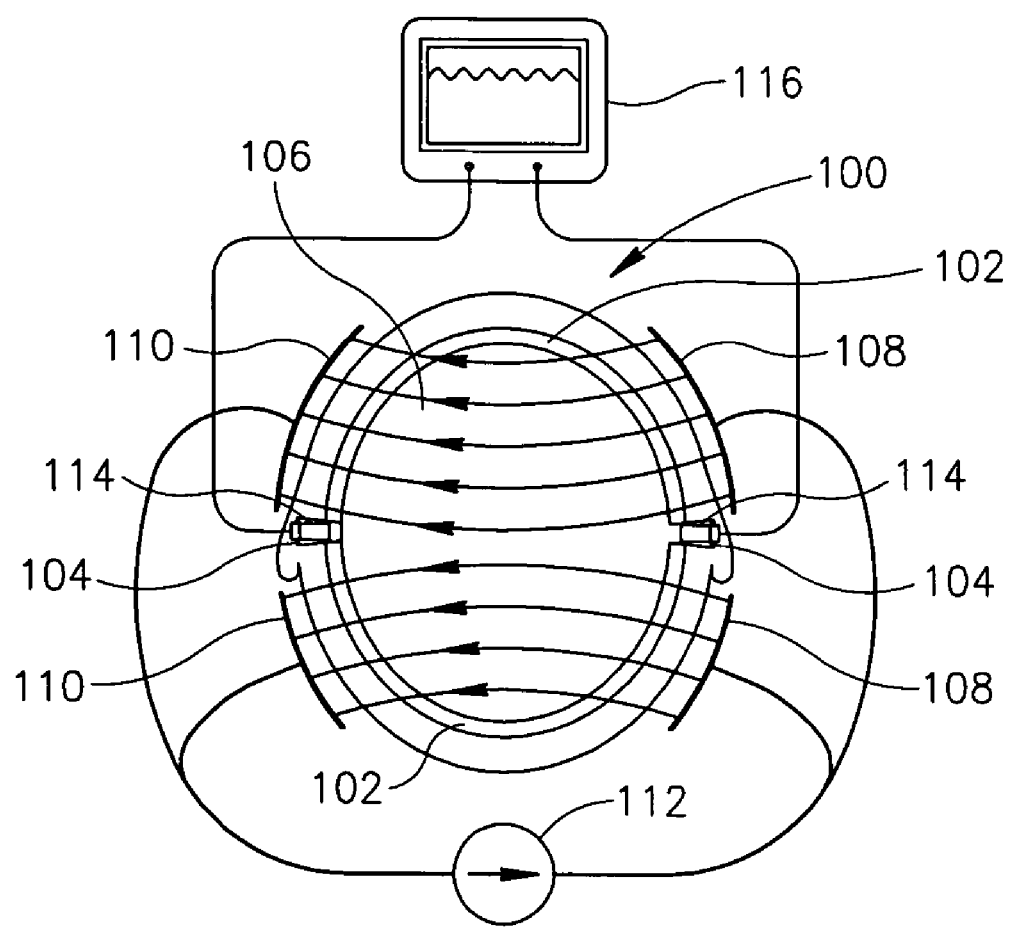
FIG. 1A is a schematic cross-sectional view of a head with electrodes, according to an exemplary embodiment of the invention.

FIG. 1 shows a cross-section of a head 100 seen from the top, including a skull 102 with two openings 104 associated with the ears, and an interior region 106 which includes the brain. It is desired to measure changes in the electrical impedance of interior region 106, without having the measurements dominated by the much greater impedance of the skull. Two positive current-carrying electrodes 108 are shown in contact with the skin on the right side of the head, one in front of the ear and one behind the ear. Similarly, two negative current-carrying electrodes are shown in contact with the skin on the left side of the head. This may be varied, for example there is only one electrode on each side, or there are more than two electrodes on each side, or the electrodes are above or below the ears, or on the ears, and the number of positive electrodes need not equal the number of negative electrodes. Having a large area of the cranium, for example 2% or 5% or 10% or more of the surface of the head, covered by electrodes, keeps a significant amount of the current flowing through the interior of the head, and reduces the amount of current that bypasses the interior of the head by flowing through the scalp. This is facilitated by having more than one electrode on each side, or by having large electrodes, which conform or can be made to conform to the curvature of the head. Optionally, instead of having one large electrode on each side of the head, or several small electrodes at the same voltage on each side covering a large total area, there is, on at least one side of the head, an annular electrode with a wide diameter, even if it has a thin annulus with a small total area. Optionally, there is also an electrode, not necessarily large, in the center of the annular electrode, with the same voltage, and optionally the annulus has one or more breaks in it. Alternatively or additionally, there are a plurality of electrodes spread out over a large area, with the same voltage, even if the total area of the electrodes themselves is small. The current will tend to be focused to go through the interior of the head, rather than through the scalp, as if the whole area inside the annular electrode, or the whole area covered by the spread out distribution of electrodes, were one large electrode. All of these options can be used on either one or both sides of the head.

Optionally, the electrode configuration causes at least 90% of the current to go through the interior of the head. Alternatively, at least 50% of the current goes through the interior of the head, or at least 20%, or at least 10%, or at least 1%. Having a significant amount of current going through the interior of the head means having enough current going through the interior of the head so that the impedance measurements are sufficiently dependent on blood volume that they can be used to measure the blood flow.

Optionally, electrodes 108 and 110 are kept in good electrical contact with the skin by a conductive gel, such as those used in ECG measurements.

A constant current is driven from electrodes 108 to electrodes 110 by power supply 112. Alternatively power supply 112 produces a constant voltage, or some combination of constant voltage and constant current, but the current is measured. Optionally, different electrodes, even on the same side of the head, have different voltages applied to them by the power supply, in order to produce a desired distribution of current flowing through the head. For example, current could be concentrated in one region of the brain, to measure blood flow in that region, or current could be distributed uniformly to measure global blood flow. Optionally, the current density is more than twice as great in one region of the brain than it is in other regions. Alternatively, the current density is 50% greater, or 20% greater, or 10% greater, in one region of the brain than in other regions. The current distribution in the brain produced by different shapes, sizes, locations and voltages of electrodes are optionally evaluated using finite element analysis software, or any other numerical or analytic method known to the art.

Although the foregoing description, and the arrow shown in power supply 112, suggest that DC current is applied to the head, in practice, for safety reasons, AC current is generally applied, optionally at frequencies between 20 and 100 kHz, and the "positive" and "negative" electrodes 108 and 110 in FIG. 1 really represent two different phases of the AC voltage applied by the power supply, 180 degrees apart. Optionally, there are three or more electrodes to which three or more different phases of AC voltage are applied. For safety reasons, and to avoid nerve stimulation, the current is optionally limited, for example to 0.5 milliamperes or 1 milliampere, depending to some extent on the area and location of the electrodes. This is a potential advantage of using a constant current rather than a constant voltage power supply. Optionally, the current is not too much lower than this, for example not less than 0.1 milliampere, since the impedance measurement may be less accurate at lower current. Optionally, the current is applied at frequencies between 20 and 40 kHz, which is high enough to run the maximum current safely, but is still low enough so that the current is largely confined to the blood and other extracellular fluid, and is excluded from the interiors of cells by the high resistance cell membranes. This makes the measured impedance maximally sensitive to blood volume.

Optionally, the current is run between 70 and 100 kHz, instead of or in addition to 20 to 40 kHz. In the higher frequency range, the cell membranes may already begin to short out due to their finite capacitance, and a significant amount of the current may flow inside the cells, as well as in the blood and extracellular fluid. Although the impedance may be somewhat less sensitive to changes in blood volume in the higher frequency range, the spatial distribution of current may be different than at lower frequency, due to the inhomogeneous distribution of blood and extracellular fluid throughout the brain. Obtaining impedance data at high frequency, especially if it supplements data obtained at lower frequency, may provide additional data about the distribution of blood flow in the brain, or the distribution of pooled blood from a cerebral hemorrhage, for example. Optionally, the current is also run at intermediate frequencies, 40 to 70 kHz, to provide additional data on blood distribution, or is only run at intermediate frequencies.

In an exemplary embodiment, voltage-measuring electrodes 114 are inserted into the ears through openings 104, reaching locations that are relatively well connected electrically with the interior of the skull, and measure the voltage across the interior of the head associated with the current flowing between current-carrying electrodes 108 and 110. Optionally, electrodes 114 are conical Ag/AgCl electrodes padded with a sponge soaked in a conductive gel. The conical shape prevents the electrodes from pressing against and possibly damaging the ear drums, when they are pushed with some force into the ear canals in order to make good electrical contact. Alternatively, electrodes 114 are shaped like the ear canal, similar to hearing aids, or are soft enough so that they conform to the shape of the ear canal, but making the electrodes relatively rigid has the potential advantage that they may stay in contact with the skin better. Optionally, the ear canal between electrodes 114 and the ear drum is completely or partially filled with a conductive gel, or another conducting fluid-like material. Optionally, there are also voltage-measuring electrodes placed just behind the ear, which are shorted to the voltage-measuring electrodes placed in the ear canal, to provide a greater total electrode area, and to spread out the electrode area more. Electrodes 114 are attached to a high impedance recording device 116, so very little current flows through electrodes 114. This means that the voltage measured by recording device 116 depends mostly on the voltage drop across the interior of the head produced by power supply 112, and does not depend very much on the impedance of the skull, or on the impedance associated with the contact between electrodes 114 and the head, or between electrodes 108 or 110 and the head. If the voltage were instead measured between electrodes 108 and 110, then the voltage might be dominated by the skull, or by the contact between the electrodes and the skin. Alternatively, electrodes 114 are not placed inside the ears, but on the surface of the head. Even in this case, depending on the dimensions and placement of electrodes 108, 110 and 114, and on the thickness of the skull, the voltage measured by recording device 116 is not sensitive to the voltage drop across the skull, or at least is less sensitive to the voltage drop across the skull than if the voltage were measured between electrodes 108 and 110, and the voltage measured by recording device 116 is sufficiently sensitive to the impedance of the interior of the head that changes in blood volume can be detected. In particular, if the diameter of the current-carrying electrodes, and the distance from the current-carrying electrodes to the voltage-measuring electrodes, is at least a few times greater than the thickness of the skull, then the potential of the voltage-measuring electrodes will tend to be substantially closer to the potential of the brain surface than to the potential of the current-carrying electrodes, on that side of the head. In some embodiments, electrodes 114 are placed on the temples, where the skull is thinner than at most other parts of the head, in order to make the voltage measured by recording device 116 less dependent on the skull impedance, and more sensitive to the impedance of the interior of the head. In other exemplary embodiments, voltage-measuring electrodes 114, or current-carrying electrodes 108 and 110, or both, are placed on the temples, or over the eye sockets, for example over the eyelids when the eyes are closed, or at the base of the skull near the foramen magnum, or over any combination of these locations.

Figure 1B:
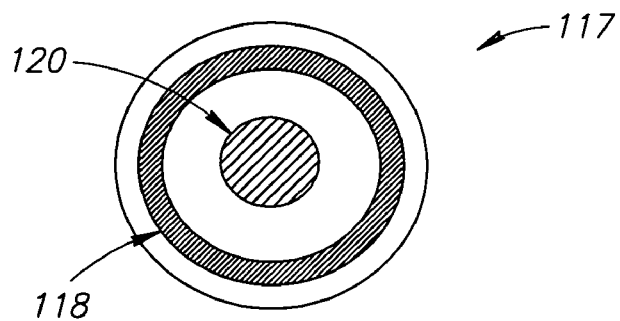
FIGS. 1B, 1C, and 1D are drawings of the surface of an electrode structure, which surface is to be placed facing the skin, according to three other exemplary embodiments of the invention.

In an exemplary embodiment of the invention, as shown in FIG. 1B, the current-carrying electrode and voltage-measuring electrode on one side of the head are part of a single electrode structure 117, for example in the shape of a flat disk. In one example, an annular current-carrying electrode 118 surrounds a central voltage-measuring electrode 120, separated from it by an annular insulating region. FIG. 1B shows the face of electrode structure 117 which is in contact with the skin. The relatively broad spread of the current-carrying electrode allows more current to go through the high impedance of the skull into the low resistance of the brain, while less current travels through the low impedance vascularized layer of the scalp, where it might bypass the skull and brain. To the extent that the diameter of the current-carrying electrode is comparable to the thickness of the scalp and skull, or at least comparable to the thickness of the scalp, the voltage-measuring electrode will tend to be relatively insensitive to the large voltage drop across the high resistance epidermis and skull, and relatively more sensitive to the voltage drop across the brain. For example, electrode structure 117 is 1 cm in diameter, or 2 cm in diameter, or 5 cm in diameter. The voltage-measuring and current-carrying electrodes have proportional dimensions similar to those shown in FIG. 1B, or alternatively have different dimensions. In an exemplary embodiment of the invention, the other side of the disk has separate contact points, connected respectively to the current-carrying and voltage-measuring electrodes, suitable for attaching electrical leads, which are connected in turn to power supply 112 and recording device 116. Alternatively, integral lead wires are provided. Optionally, electrode structures like that shown in FIG. 1B are used on both sides of the head.

Figure 1C:
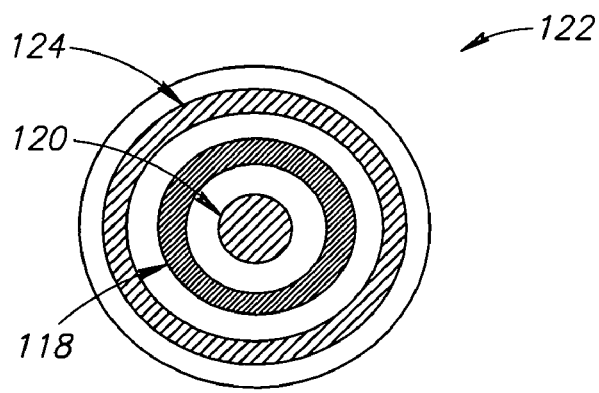

In an alternative embodiment, instead of electrode structure 117, electrode structure 122, shown in FIG. 1C, is used. There is an annular current-carrying electrode 118, and a central voltage-measuring electrode 120, as in electrode structure 117, but there is a second voltage-measuring electrode 124, outside current-carrying electrode 118, and optionally electrically shorted to central voltage-measuring electrode 120. Electrode structure 122 is, for example, 1 cm in diameter, or 2 cm, or 5 cm, or has a smaller or larger diameter. The relative proportions of the electrodes need not be the same as the exemplary proportions shown in FIG. 1C. The broader spread of the voltage-measuring electrode, compared to electrode structure 117, may make the voltage measurement even less sensitive to the voltage drop across the epidermis and skull. Furthermore, the broad spread of the voltage-measuring electrode, which is at a constant potential, may tend to reduce radial electric fields and radial currents in the scalp, and cause a greater portion of the current to flow through the interior of the head, similar to the effect of a broadly spread out current-carrying electrode.

Figure 1D:
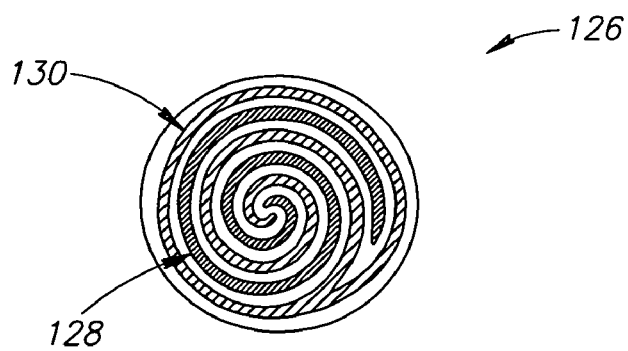

In an alternative embodiment, an electrode structure 126, shown in FIG. 1D, is used. This structure has a spiral shaped current-carrying electrode 128 intertwined with a spiral shaped voltage-measuring electrode 130. Depending on the details of the geometry, electrode structure 126 potentially provides a greater surface area for the current-carrying electrode than electrode structures 117 or 122, thereby providing a more focused pattern of current flow through the interior of the head, and making better use of the available surface area. The greater surface area for voltage-measuring electrode 130 may provide similar benefits. As long as the widths of the different arms of the electrodes, and the spacing between them, are at least comparable to the thickness of the scalp and/or the skull, the voltage-measuring electrodes will tend to be relatively insensitive to the voltage drop in the scalp and/or the skull, as well as to any voltage drop between the current-carrying electrodes and the skin, due to poor contact, and will be relatively more sensitive to the voltage drop across the brain. For example, adjacent turns of the spirals in FIG. 1D are spaced 1 mm apart, or 2 mm, or 5 mm, and electrode structure 126 has a diameter of 1 cm, or 2 cm, or 5 cm. Electrode structures with a variety of geometric configurations, which meet these criteria, may provide benefits similar to those provided by one or more of electrode structures 117, 122, and 126.

Optionally, any combination of electrode structures 117, 122 and 126 is used, as well as separate current-carrying and voltage-measuring electrodes as shown, for example, in FIG. 1A. Optionally, more than two electrode structures are placed on the head, but, optionally, only two of them are used at a time to produce current and measure voltage. These two electrode structures, or separate sets of electrodes, need not be placed symmetrically on opposite sides of the head, but, for example, one could be placed over an eye socket, and one near an ear. Placing the electrode structures in different locations may give information about the impedance in different regions of the head. When electrodes are placed over an eye socket, the eye is preferably closed, for example because the patient is unconscious, and the electrodes are placed over the eyelid.

Optionally, electrode structures such as those shown in FIGS. 1B, 1C, and 1D, or separate electrodes such as those shown in FIG. 1A, are placed over or near openings or thin areas of the skull, for example the ears, the eye sockets, the temples, and the foramen magnum. Optionally, the electrode structures or separate electrodes are not rigid flat disks, but are flexible enough to be molded to fit the shape of the head in those regions, or are relatively rigid but are molded to fit the shape of the head in those regions, optionally with some flexibility to allow them to be adjusted to slightly different head shapes in different individuals, with conductive gel used to fill in any small gaps. The stiffness of the electrode structure, and the manner in which it is attached to the skin, optionally depends on where it is attached. For example, a softer electrode structure, exerting less pressure, may be used over the closed eyelids, than is used over the temples, to avoid discomfort or damage to the eyes. Optionally, the conductive gel does not cover the entire face of the electrode structure, but is applied only on and near the electrodes themselves, or only on and near the current-carrying electrodes, so that a current-carrying electrode is not shorted to an adjacent voltage-measuring electrode.

Optionally, the electrodes come in different sizes and/or shapes for use on different people, for example adults and children. Optionally, different people may use the same size and shape of electrode, but different parts of the electrode make good contact with the skin in different people.

Dividing the voltage measured by recording device 116 by the current produced by power supply 112 gives a measure of the electrical impedance of interior region 106, which is related to the blood volume in the brain. Optionally, the voltage produced by power supply 112 is used in addition to, or instead of, the voltage measured by recording device 116 in calculating the impedance, possibly as a check on the reasonableness of the voltage measured by recording device 116. But often, the voltage produced by power supply 112 is influenced more by the skull impedance, and less by the impedance of the interior of the head, than the voltage measured by recording device 116. If AC current is used, then of course the current and voltage are each expressed by a complex number, representing the amplitude and phase. At very high frequencies, for example above about 100 kHz, the capacitance of the cell membranes will start to look like a short circuit, and current will flow almost as easily through the cells as it flows through the blood and other fluid surrounding the cells. At these high frequencies, the impedance of the head will be less sensitive to blood volume than it is at lower frequencies, because it will depend on the total volume of the brain, including the cells, not just on the volume of the blood and the extracellular fluid. Optionally, for this reason, frequencies below about 100 kHz are used to measure the impedance of the head. Optionally, measurements of the relative phase of the voltage measured by recording device 116 or by power supply 112, and the current produced by power supply 112, particularly at higher frequencies such as 100 kHz, are used to measure the impedance of the head. Such phase measurements are potentially useful at frequencies comparable to 100 kHz, where the impedance of the head has a substantially capacitive component due the cell membranes, especially if the capacitive part of the impedance is insensitive to blood volume, or has a different dependence on blood volume than the resistive impedance of the head. Even if the measured impedance is affected to a large degree by undesired effects such as the skull impedance, or the capacitance of the cell membranes, the measured impedance is still useful for measuring blood volume if it depends significantly on blood volume as well.

Optionally, the impedance is never actually calculated, but the blood volume is determined directly from the voltage data, particularly if the current produced by power supply 112 is always the same. Alternatively, feedback to the power supply is used to keep the voltage measured by recording device 116 constant (i.e. constant amplitude and phase), and the current produced by power supply 112 is used directly to determine the blood volume. Variants on these methods, for example, keeping some linear combination of voltage and current the same, will be apparent to those skilled in the art.

Figure 2A:
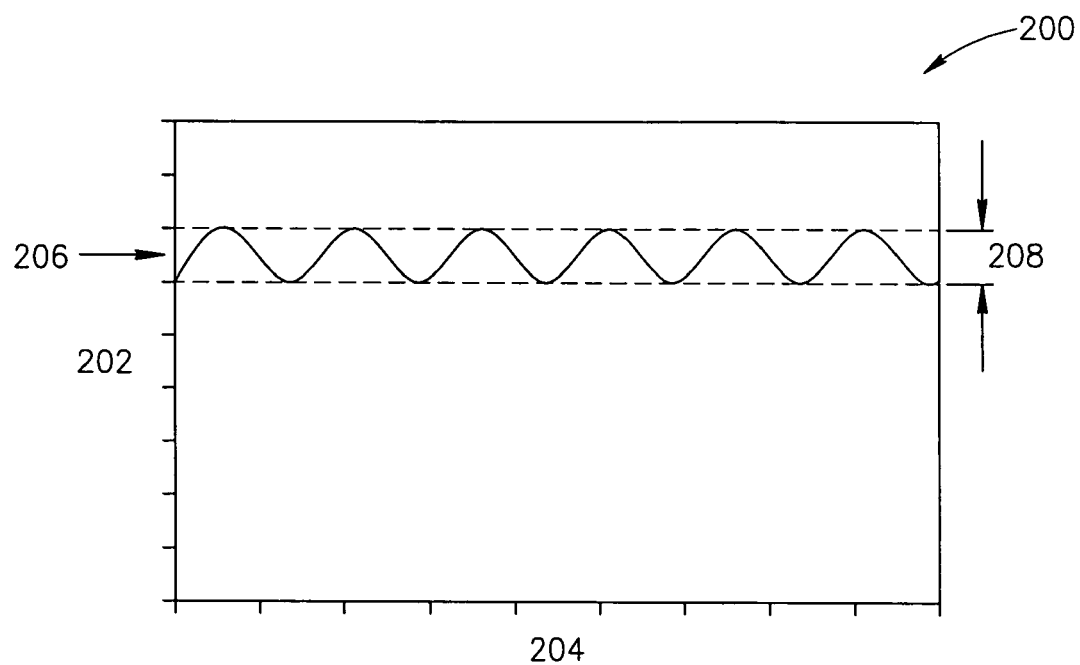
FIG. 2A is a schematic plot of typical impedance data according to the same or a different exemplary embodiment of the invention than those shown in FIGS. 1A-1D.

FIG. 2A shows a plot 200 of resistive impedance vs. time, measured as described in FIG. 1, over a period of time covering several pulse cycles. The vertical axis 202 represents impedance, or resistance, and the horizontal axis 204 represents time. The average resistance R over time has a value given by level 206 on the vertical axis, and the variation in resistance $\Delta R$, associated with the pulse cycle, is shown by interval 208. The resistance decreases during the systolic phase of the pulse, when the blood volume V of the brain is higher, and increases during the diastolic phase when the blood volume V is lower. The relative change in blood volume over a pulse period $\Delta V/V$ is comparable to $\Delta R/R$. If desired, the exact relation between $\Delta V/V$ and $\Delta R/R$ can be calibrated for a given configuration of electrodes by comparing measured values of $\Delta R/R$ with measurements of blood flow performed by other means known to the art. The blood flow to the brain is found by multiplying $\Delta V/V$ by the total brain blood volume V (estimated, for example, from a known average value for humans) and the pulse rate.

Even if a calibration is not done, or even if the calibration is not accurate if applied to a different patient from the calibrated patient, the estimated values of blood flow obtained by this technique are still adequate for some applications of interest, such as determining whether CPR is working at all, or detecting a sudden decrease in blood flow to the brain during surgery. If CPR is not being administered properly, or if blood flow to the brain is reduced by a stroke or another sudden event suffered during surgery, then the blood flow to the brain may be essentially zero, or much lower than normal, and this may be detected even if the technique does not measure absolute values of blood flow very accurately.

Figure 2B:
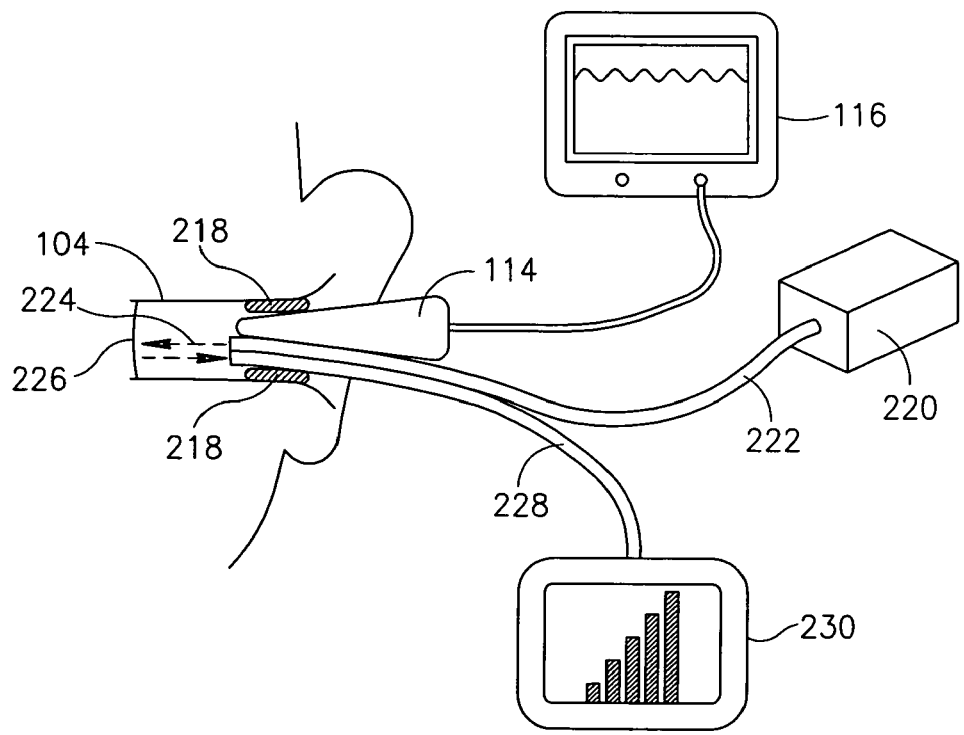
FIG. 2B is a schematic cross-sectional view showing an electrode and an optical probe inserted into an ear.

FIG. 2B shows a closeup view of voltage-measuring electrode 114 inserted into ear canal 104. Electrode 114 is connected to recording device 116, which analyzes the voltage data and displays information about the head impedance and the blood flow. Electrode 114 is surrounded by a sponge 218, soaked in an electrically conducting gel. Electrode 114 is conical in shape, and too wide at the base to reach the ear drum when it is inserted into the ear. Optionally, there is a system for doing optical measurements of blood flow in the ear, combined with electrode 114. A light source 220, for example a red or infrared laser or laser diode, sends light through optical fiber 222. Light ray 224 reflects off a surface 226 inside the ear, for example the ear drum, or another surface whose color is affected by blood flow and/or oxygenation of the blood. Sponge 218 holds optical fiber 222 firmly enough in place so that if the measurements are repeated, light ray 224 always reflects from substantially the same place, so any changes in reflectivity are due to changes in blood flow or oxygenation, rather than due to fiber 222 changing its position or orientation. The reflected light goes into another optical fiber 228, which carries it to an analyzer 230. Fiber 228 is also held firmly in place by sponge 218. Analyzer 230 uses information about the reflectivity of surface 226 to measure or estimate blood flow rate, and/or the degree of oxygenation of the blood, and optionally displays the information. Analyzer 230 and light source 220 are optionally based on any existing system of photoplethysmography, known to those skilled in the art. Optionally, a fiber optic cable, comprising a plurality of optical fibers, is used instead of optical fiber 222 and/or optical fiber 228. Optionally, fibers 222 and 228 are bundled together with the wire connecting electrode 114 to recording device 116. Optionally, analyzer 230 is packaged together with recording device 116. Optionally, data from analyzer 230 is combined with data from recording device 116, and a single estimate of blood flow is displayed, based on the combined data. Optionally, a probe comprising fibers 222 and 228, and sponge 218 or a similar element to hold the probe in place, is used for optical measurements in the ears, even if voltage-measuring electrodes 114 are not placed in the ears.

Figure 3A:
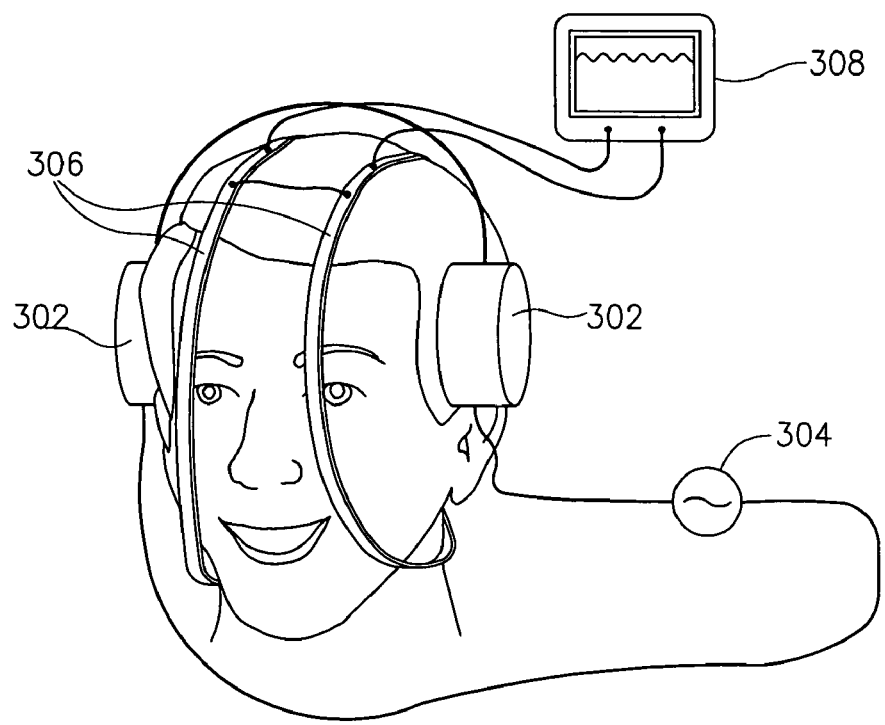
FIGS. 3A, 3B, and 3C are schematic perspective views of a head with induction coils according to three other exemplary embodiments of the invention.
Figure 3B:
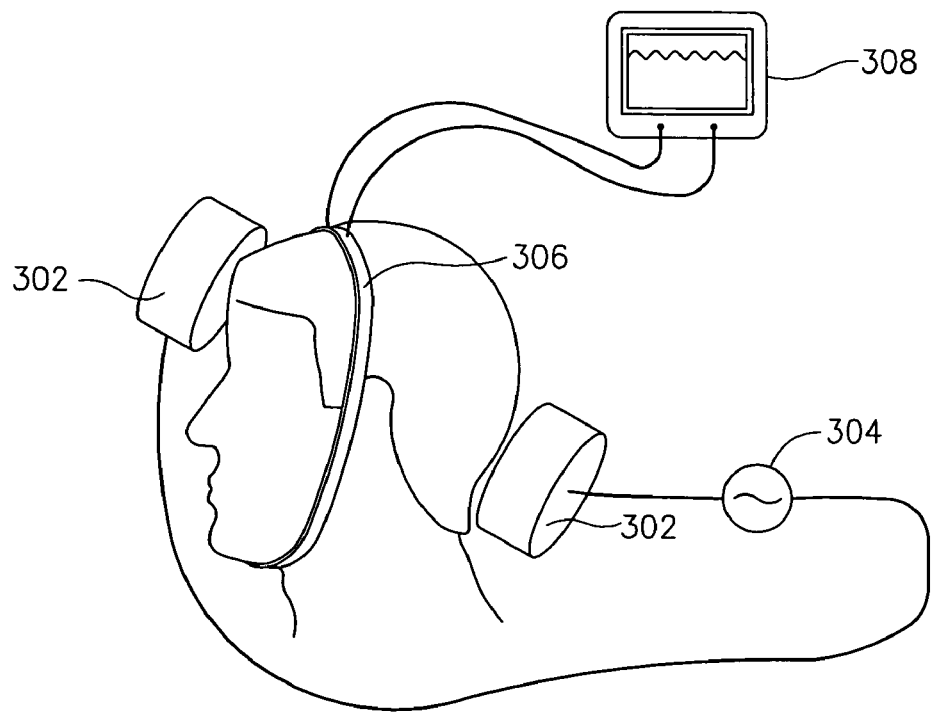
Figure 3C:
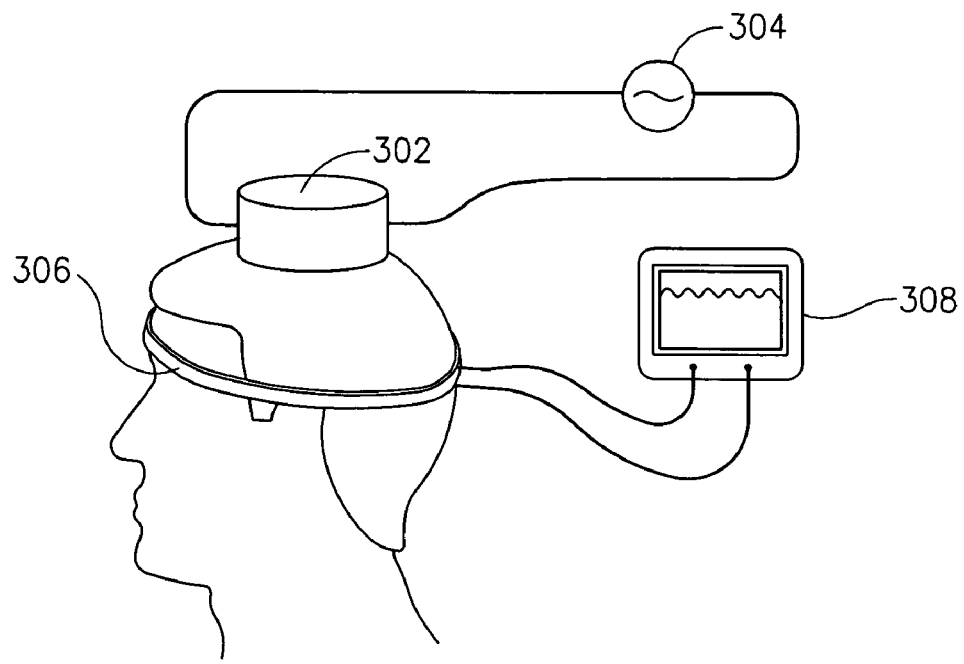

A different method of inducing currents in the brain and measuring voltages is illustrated in FIGS. 3A, 3B, and 3C, which show coils placed around the head in different orientations, to induce currents in the brain. Other magnetic induction methods may be used as well, including different coil configurations, or the use of rotating or oscillating permanent magnets or electromagnets to produce time-varying magnetic fields in the head. Measuring the induced currents, by measuring their effects on the induced magnetic and electric fields, gives information about the impedance of the brain, and hence the blood volume of the brain. In FIG. 3A, coils 302, one on each side of the head, have AC current flowing in them, driven by power supply 304, and generate an AC magnetic field inside the head. The changing magnetic flux induces electric fields in the head which are parallel to the currents in coils 302, but in the opposite direction. The AC magnetic field optionally is large enough so that the induced electric fields are large enough to produce measurable effects, as discussed below, but small enough not to produce peripheral or central nerve stimulation. Optionally, the threshold for nerve stimulation is increased by using trains of short pulses, or other methods known to the art, so that higher AC magnetic fields can be used. The induced electric fields cause eddy currents to flow in the brain, of an amplitude which depends on the impedance of the brain. The eddy currents in turn generate their own magnetic field and an associated induced electric field, reducing the magnetic flux inside the brain. Coils 306 measure a voltage associated with the AC magnetic flux produced by coils 302, and this voltage is recorded by recording device 308. The reduction in magnetic flux caused by the eddy currents flowing in the brain can be detected by recording device 308, since the induced voltage will be lower, i.e. the mutual inductance between coils 302 and coils 306 will be reduced. The eddy currents will also give the mutual inductance an imaginary (dissipative) part, which may be easier to detect than the reduction in the real part of the mutual inductance. An estimate of the absolute impedance of the brain may be made by observing how the mutual inductance of coils 302 and 306 changes with the frequency of the AC current. Even without making such an absolute estimate of the impedance of the brain, changes in impedance of the brain over time, during the pulse cycle, may be detected by observing the changes in mutual inductance during the pulse cycle.

Optionally, the electric fields induced by coils 302 are measured by electrodes placed on or in the head, similar to the voltage-measuring electrodes shown in FIGS. 1A and 2B. The electrodes are shaped and sized, for example, to be placed in the ears or in the nose, or to be placed on the temples or elsewhere on the head, with electrically conducting gel. The induced electric field depends on the impedance of the brain, because it is modified by the eddy currents which depend on the impedance of the brain.

Here are some considerations used in choosing the frequency of the AC current in coils 302. For a brain resistivity of 2 ohm-meters, typical of body tissue, the magnetic field produced by the eddy currents, which depends on the impedance of the brain, will be comparable to the magnetic field produced by the induction coils when the skin depth of the brain is comparable to its radius, about 10 cm. This occurs at a frequency of about 50 MHz. At frequencies well above 100 kHz, however, the impedance of the cell membranes may be effectively shorted out, so that current flows freely inside as well as outside the cells, so the resistivity of the brain is somewhat lower, and eddy currents become important at about 30 MHz. The impedance of the brain at such high frequencies is less sensitive to blood volume than it is below 100 kHz, due to the conduction pathway going inside the cells, but the impedance is still somewhat sensitive to blood volume, since the total volume of fluid in the brain, inside and outside cells, still increases when the blood volume increases. Optionally, frequencies of about 10 MHz, or a few tens of MHz, or even about 100 MHz, are used, since the blood volume may have the greatest effect on eddy currents in this frequency range. At frequencies well above 30 MHz, eddy currents may largely exclude magnetic flux from the interior of the brain, and the mutual inductance of the coils may be less sensitive to blood volume. Optionally, the frequencies used are low enough so that the eddy currents do not reduce the magnetic field at any point inside the head by more than a factor of 1.5. Alternatively, the eddy currents do not reduce the magnetic field by more than a factor of 3, or by more than a factor of 6. At frequencies well below 30 MHz, the small change in the real part of the mutual inductance might be difficult to detect, but the change in the dissipative part, which is proportional to frequency well below 30 MHz, might be relatively easy to detect, even below 100 kHz, if it is the dominant dissipative term. Optionally, frequencies between a few tens of kHz, about 100 kHz, or a few hundred kHz are used, since they are easier to work with than frequencies of a few tens of MHz, and may still provide sufficient sensitivity to blood volume. Alternatively, frequencies of a few hundred kHz, about 1 MHz, or a few MHz are used, since they may provide the best trade-off between sensitivity and ease of use.

Eddy currents at different frequencies may have different spatial distributions in the brain, both because of skin effects (differing mostly at frequencies above 1 MHz), and because of the finite capacitance of cell membranes (differing mostly at frequencies below 1 MHz). Eddy currents may also have a different distribution in the brain than currents produced by electrodes placed on the head. Different distributions of current may provide different data about the distribution of blood in the head, for example in a patient with a cerebral hemorrhage where blood can pool locally at one or more locations. Optionally, eddy currents are induced at more than one frequency, or both coils and electrodes are used to induce currents in the brain, in order to obtain more data about the distribution of blood in the brain.

Optionally, the currents in induction coils 302 are of a magnitude small enough not to cause peripheral or central nerve stimulation, or to cause deleterious health effects or discomfort from heating of the brain or other body tissues. The maximum safe currents, which depend on the frequency and duration of the currents, are well known to those skilled in the art, in the field of magnetic resonance imaging for example. Optionally, the currents used are only a few times less than the maximum safe currents, or even only a few percent less than the maximum safe currents, and not many times less, in order not to sacrifice precision of the measurements.

Optionally, instead of using separate coils 306 to detect the induced voltage, coils 302 are used to detect the induced voltage, i.e. the self-inductance of coils 302 is used, instead of the mutual inductance between coils 302 and 306. However, a possible advantage of using mutual inductance rather than self-inductance is that the voltage in coils 306 will not be sensitive to the resistance of coils 302, or the resistance of coils 306 if recording device 308 has a high impedance. In particular, the dissipative part of the mutual inductance may be the dominant dissipative term in the voltage measured the recording device 308, making it easy to measure. On the other hand, if self-inductance of coils 302 were used, the dissipative part of the inductance would likely be small compared to the resistance of the coils, and difficult to measure.

Alternatively or additionally, the magnetic fields produced by the coil currents and by the eddy currents in the brain are measured by magnetic sensors such as Hall sensors, flux gate magnetometers, or SQUIDs. Such magnetic sensors will give more local magnetic field measurements than large coils encircling the head, and may give data that is weighted toward local changes in blood flow, possibly complementing the more global data from large coils. Global data is also optionally obtained by averaging the results from several local magnetic sensors.

FIG. 3A shows two coils 302 on the sides of the head, and two coils 306, near the midplane of the head, but going around opposite sides of the neck. However, the coils need not be arranged symmetrically as shown. Optionally, there is only one coil 302, or only one coil 306. Optionally, coils 302 are close to the midplane of the head, and coils 306 are located on the sides of the head. An optimal configuration of coils can optionally be found by using magnetic finite element methods, or other numerical or analytic methods known to the art.

FIGS. 3B and 3C show coils 302 and 306 oriented in other directions with respect to the head. In addition to obtaining adequate mutual inductance between the coils, and adequate dependence of the mutual inductance on the impedance of the brain, another consideration in choosing the coil orientation is the ability to keep the coils positioned rigidly with respect to the head. Changes in position of the coils will affect their mutual inductance and self-inductance, and may appear as spurious changes in calculated brain impedance.

Figure 4:
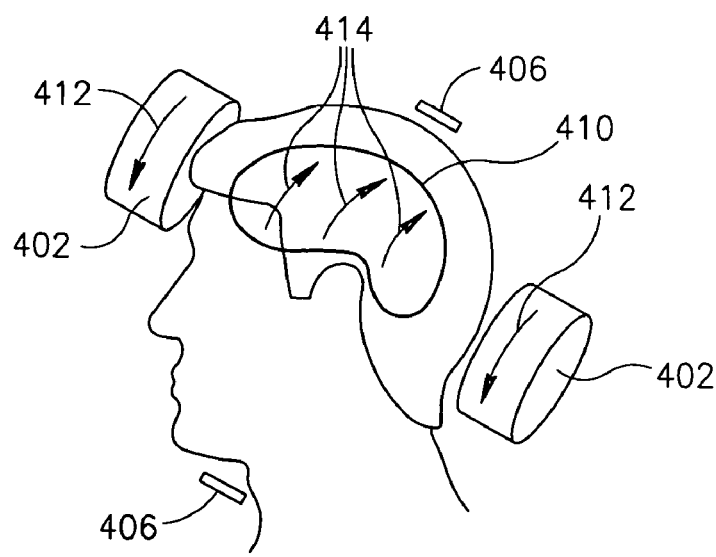
FIG. 4 is a schematic view of the head showing the brain and induction coils, according to the same embodiment of the invention as FIG. 3B.

FIG. 4 shows coils 402 arranged in front and back of a head, as in FIG. 3B, and a coil 406 going around the head from to top to under the chin, to measure the flux induced by coils 402. The brain 410 is shown inside the head. When currents 412 in coils 402 are flowing in one direction, induced eddy currents 414 flow in the brain in the opposite direction, but the two currents are less than 180 out of phase. (Similar induced eddy currents in the brain would also be seen with the coil configurations shown in FIG. 3A or 3C, but the currents would be flowing in different directions, generally opposite to the currents flowing in the coils.) Currents 414 reduce the magnetic flux inside the brain, and reduce the total flux passing through coils 402 and 406. Currents 414 also change the phase of the flux passing through coils 402 and 406, relative to the phase of current 412 in coils 402. This change in amplitude and phase of the flux is detected by coil 406 as a change in the amplitude and phase of the voltage of coil 406, relative to the amplitude and phase of current 412. Thus the amplitude and phase of the voltage in coil 406 provides information about the impedance of brain 410.

Optionally, a C-shaped element of high magnetic permeability, not shown in the drawings, extends between the two coils 302 in any of FIG. 3A, 3B, or 3C, in order to increase the magnetic field induced in the brain, for a given current in coils 302. This would reduce the size and cost of the required power supply, and reduce the ohmic heating of the coils, to produce a given magnetic field and induced electric field in the brain. Such a C-shaped element could, however, have the potential disadvantage of introducing an additional source of dissipation, due to eddy currents and hysteresis in the magnetic material, that might make it more difficult to detect the eddy currents introduced in the brain by coils 302, and many high permeability alloys have lower permeability at high frequencies, especially above 1 MHz. Optionally the C-shaped element is laminated, to reduce eddy currents and increase the effective permeability at a given frequency. Optionally, the C-shaped element is made of vanadium permendur, or a similar alloy with low magnetic anisotropy, because its permeability may not fall off as much at high frequencies as is the case with other high permeability materials.

Figure 5A:
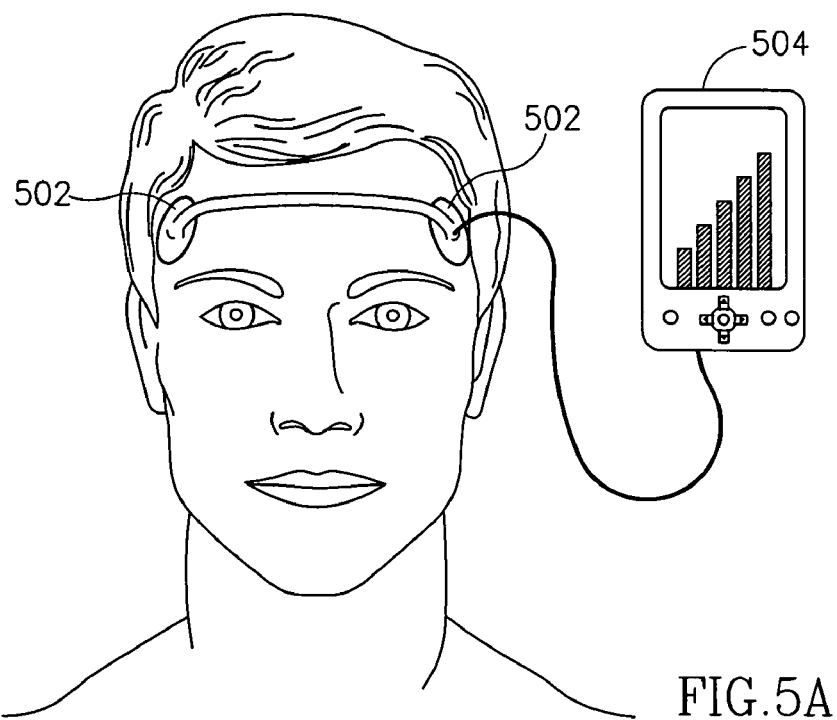
FIGS. 5A, 5B, and 6 are perspective views of a head with electrodes, and a monitor, according to three different exemplary embodiments of the invention.
Figure 5B:
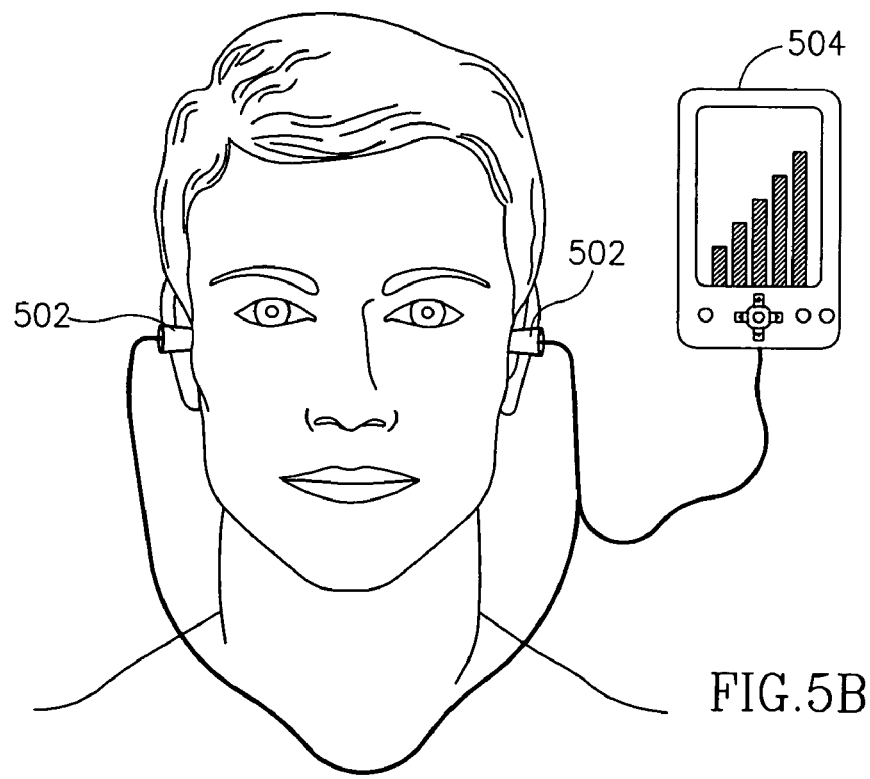

FIGS. 5A and 5B illustrate portable embodiments of the invention that are potentially suitable for use in the field, in contrast to non-portable embodiments of the invention that are suitable for use in a hospital setting during surgery, for example. Assemblies 502 contain both current-carrying and voltage-measuring electrodes, either placed on the temples, as in FIG. 5A, or on the ears, and with the voltage-measuring electrodes optionally inserted into the ears, as in FIG. 5B. Optionally, assembly 502 on each side of the head covers the ears, resembling earmuffs, with current-carrying electrodes outside the ears and voltage-measuring electrodes inside the ears. Optionally, there is more than one current-carrying electrode on each side. Optionally, some of the electrodes are placed on the temples or elsewhere on the head, and some of them are placed on or in the ears.

Alternatively or additionally, assemblies 502 contain coils which induce eddy currents in the brain, and coils or other magnetic sensors which detect the eddy currents. Optionally, if assemblies 502 contain coils, they are substantially bigger than shown in FIGS. 5A and 5B, in order to produce a magnetic field that is more uniform in the brain, rather than concentrated near the assemblies, and in order to reduce the ohmic power generated by the coils when producing a given magnetic field. Alternatively, the coils are small, and are inserted into the ears, particularly for making local measurements of impedance near the ears.

Monitor 504 optionally displays the blood volume or blood flow rate as a function of time, determined from the impedance measurements. Alternatively or additionally, monitor 504 has warning lights, for example a green light which lights up when the blood flow rate to the brain is satisfactory, and a red light which lights up, and/or a buzzer which sounds, when the blood flow rate is too low, or changes suddenly. Optionally, monitor 504 has five or fewer warning lights, to minimize the information that an emergency medical technician has to sift through, when looking at the monitor.

Optionally, a power supply is packaged together with monitor 504. Alternatively, there is a separate power supply, not shown in FIGS. 5A and 5B.

Figure 6:
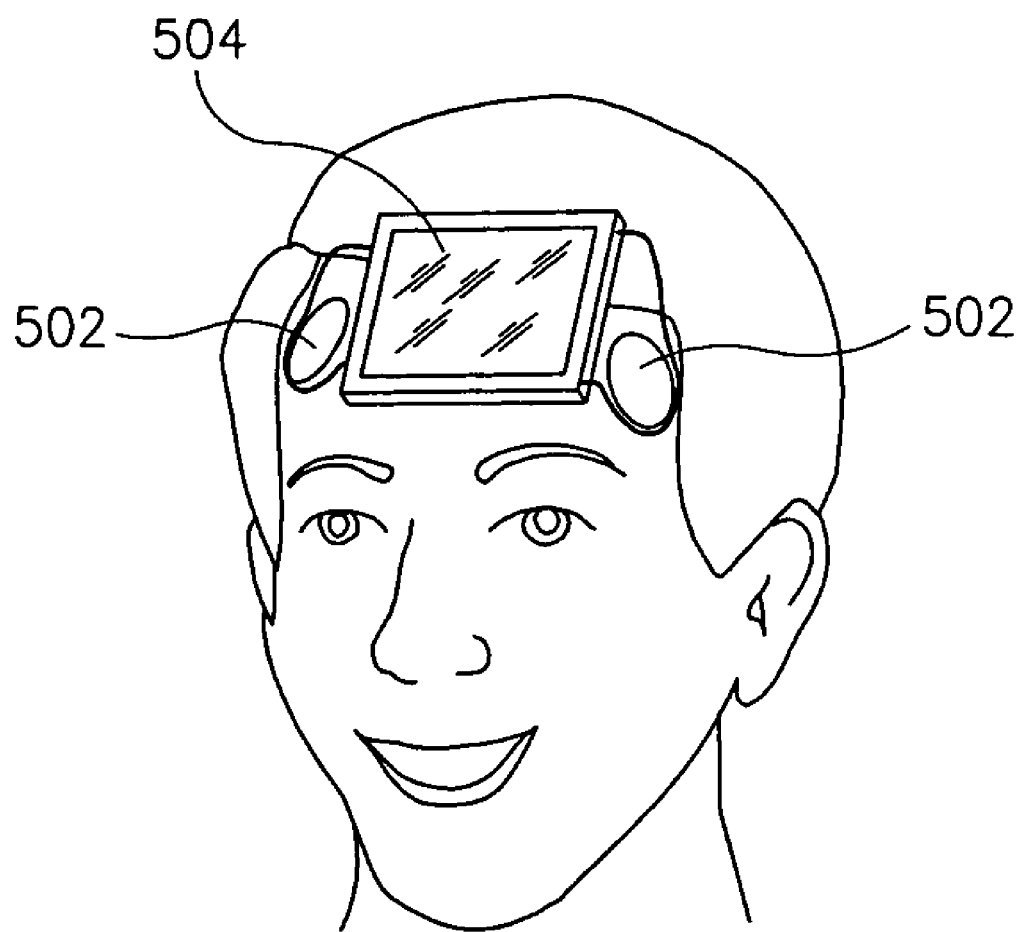

FIG. 6 shows a similar embodiment of the invention, but with monitor 504 mounted on the patient's forehead. Alternatively, there are two monitors, one mounted on the patient's forehead which, for example, has only a few warning lights, and one not mounted on the patient which displays more information.

Optionally, any of recording device 116 in FIGS. 1A and 2B, power supply 112 in FIG. 1A, analyzer 230 in FIG. 2B, power supply 304 in FIGS. 3A, 3B, and 3C, recording device 308 in FIGS. 3A, 3B and 3C, and monitor 504 in FIGS. 5A, 5B and 6, comprise a controller, which controls the currents sent to the current-carrying electrodes or coils, and analyzes the data. Optionally, the controller includes any of a CPU, power electronics, an AC/DC converter, and non-volatile memory to store software and data. Optionally, different elements of the controller are located in different places, for example the power supply and the recording device, and/or the controller or parts of the controller are packaged separately.

These portable versions could be used, for example, during the administration of CPR by emergency medical technicians, to monitor whether the CPR is being administered effectively. Studies (for example, S. Braunfels, K. Meinhard, B. Zieher, K. P. Koetter, W. H. Maleck, and G. A. Petroianu, "A randomized, controlled trial of the efficacy of closed chest compressions in ambulances," Prehosp. Emerg. Care 1997 July-September; 1(3):128-31) have shown that, in the absence of feedback, CPR is often administered ineffectively.

In any of the above mentioned embodiments of the invention, motion of the head relative to the electrodes, coils, or sensors can produce a spurious change in measured blood volume, and hence a spurious calculated blood flow. Various methods are optionally used to reduce such motion artifacts. For example, the effect of any motion that is not correlated with the pulse cycle is optionally reduced by averaging over time. Such averaging will not eliminate motion artifacts in the calculated blood flow due to motion that is correlated with the pulse, such as motion associated with the administration of CPR. Motion artifacts are also optionally reduced by keeping the head immobilized, and keeping the electrodes, coils, and sensors rigidly in place against the head. Optionally, motion artifacts are compensated for by using an accelerometer to detect motion of the head, and modeling the motion artifacts, or by only using data taken when the head is not moving too much. Additionally or alternatively, a pulse detected in the neck is used to distinguish motion artifacts from the real effects of blood flow in the brain, even if the pulse in the neck is not usable for measuring blood flow directly.

Potential applications of these techniques for measuring blood flow in the brain may best be served by adapting the device to each application. For example:

1) For emergency medical situations such as arrhythmia, myocardial infarction, cardiac arrest, or traumatic hemorrhagic shock, the device is optionally made portable, with a self-contained power supply, perhaps battery operated, and/or has a monitor with only limited information displayed.

2) For follow-up of traumatic brain injury patients, the device optionally is portable enough and rugged enough for home use, using a battery or AC power from a wall outlet, and/or has a monitor that is simple enough to be used by the patient or a family member with little training, and optionally also displays additional information that could be used, for example, by a visiting nurse.

3) For monitoring blood flow to the brain prior to and during surgical procedures, especially carotid endarectomy, the device need not be portable or could be moved around on a cart, and optionally displays data that would be of interest to the surgeon or other medical personnel in the operating room, so that changes can be made in the surgical procedure in real time, in response to a decrease in blood flow, for example.

4) For monitoring patients suffering from diseases such as stroke, syncope, and sickle cell anemia, where disturbances in cerebral blood flow often occur, the device optionally measures local blood flow in different regions of the brain, and optionally comes in different versions, one for hospital use, for example in an intensive care unit, and one for long term monitoring at home.

5) For cardiopulmonary resuscitation (CPR), to verify that it is working effectively, the device optionally integrates the blood flow in the brain after every few chest compressions, for example every time the lungs are expanded, and prominently displays the result on a large dial or array of lights, so the person administering CPR can immediately see whether the chest compressions are too weak or too strong, or too slow or too fast, or whether the heart has started beating on its own. A portable version of the device is optionally used by emergency medical technicians in the field or in an ambulance. A less portable version, on a cart for example, is optionally used in a hospital emergency room.

For these applications, accurate measurements of blood flow to the brain are not necessarily needed, but it is important to detect large changes in blood flow, or the presence or absence of blood flow. The potential for low cost of the system, and the fact that it can be used by someone with relatively little training, is important for these applications, especially for CPR. Other potential advantages of this technique over existing methods of measuring blood flow in the brain, for example TCD, include the fact that it measures blood flow continuously in real time, the fact that it operates automatically without the need for an operator whose sole function is to run the equipment, the fact that it measures global rather than local blood flow, and the small size and portability of the equipment in some embodiments of the invention.

As used herein, "two portions of a same electrode" includes the case of two separate electrodes that are electrically shorted together.

The invention has been described in the context of the best mode for carrying it out. It should be understood that not all features shown in the drawings or described in the associated text may be present in an actual device, in accordance with some embodiments of the invention. Furthermore, variations on the method and apparatus shown, which will be readily apparent to and may be readily accomplished by persons skilled in the art, are included within the scope of the invention, which is limited only by the claims. Also, features of one embodiment may be provided in conjunction with features of a different embodiment of the invention. The words "comprise", "include" and their conjugates as used herein mean "include but are not necessarily limited to".

The invention claimed is:

1. A method of monitoring blood flow in a patient's brain during surgery, comprising:
    a) performing surgery on the patient;
    b) causing currents to flow inside the patient's head by producing electric fields inside the head during the surgery, by placing at least two current-carrying electrodes on the head, and applying at least two different electric potentials to the current-carrying electrodes;
    c) measuring at least changes in the electric fields and the currents during the surgery;
    d) estimating changes in the blood volume of the head during the surgery, using a controller to analyze data of the measurements of the electric fields and the currents; and
    e) estimating blood flow in the brain during the surgery, from the changes in blood volume of the head.

2. A method according to claim 1, wherein using the measurements of electric fields and the currents comprises calculating the impedance of the head at least two different times.

3. A method according to claim 1, wherein there is more than one current-carrying electrode at the same electric potential.

4. A method according to claim 1, wherein the current-carrying electrodes are sufficiently large in area so that a significant amount of the current flows through the interior of the skull, and not through the scalp.

5. A method according to claim 1, wherein the electrodes are spread out enough in area so that a significant amount of the current flows through the interior of the skull, and not through the scalp.

6. A method according to claim 5, wherein the smallest convex area on the surface of the head which includes every current-carrying electrode of a given polarity is at least 2 cm across.

7. A method according to claim 6, wherein said area is at least 5 cm across.

8. A method according to claim 7, wherein said area is at least 10 cm across.

9. A method according to claim 1, wherein placing at least two current-carrying electrodes on the head comprises placing at least one of the electrodes adjacent to an opening in the skull.

10. A method according to claim 1, wherein placing at least two current-carrying electrodes on the head comprises placing at least one of the electrodes adjacent to a thin area of the skull.

11. A method according to claim 1, wherein measuring the electric fields comprises placing at least two voltage-measuring electrodes on the head, on a separate circuit from the current-carrying electrodes, and measuring the electric potential difference between the voltage-measuring electrodes.

12. A method according to claim 11, wherein the smallest convex area which includes all of the voltage-measuring electrodes of a given polarity is at least 2 cm across.

13. A method according to claim 12, wherein said area is at least 5 cm across.

14. A method according to claim 13, wherein said area is at least 10 cm across.

15. A method according to claim 11, wherein placing at least two voltage-measuring electrodes on the head comprises placing at least one voltage-measuring electrode adjacent to an opening in the skull.

16. A method according to claim 11 or claim 15, wherein the opening is an eye socket, and said electrode is placed over the closed lid of the eye.

17. A method according to claim 11 or claim 15, wherein the opening is an ear, and said electrode is placed in the ear canal.

18. A method according to claim 11 or claim 15, wherein the opening is the foramen magnum, and said electrode is placed near the base of the skull.

19. A method according to claim 11, wherein placing at least two voltage-measuring electrodes on the head comprises placing at least one voltage-measuring electrode adjacent to a thin area of the skull.

20. A method according to claim 10 or claim 19, wherein the thin area of the skull is the temple.

21. A method according to claim 1, wherein
    a) placing the current-carrying electrodes on the head comprises placing at least three current-carrying electrodes on the head; and
    b) applying different electric potentials to the current-carrying electrodes comprises applying at least three different electric potentials to the current-carrying electrodes so that a desired current distribution is produced in the head.

22. A method according to claim 21, wherein the desired current distribution is concentrated in a desired region of the brain, and estimating the changes in blood volume of the head comprises estimating the changes in blood volume in the desired region of the brain.

23. A method according to claim 1, also comprising using photoplethysmography on tissue inside the head.

24. A method according to claim 23, wherein the tissue is inside the ear.

25. A method according to claim 23, wherein the tissue is inside the nose.

26. A method of performing cardiopulmonary resuscitation (CPR) on a patient, while monitoring blood flow in the patient's brain to verify that the CPR is being performed effectively, comprising:
    a) performing CPR on the patient;
    b) causing currents to flow inside the patient's head by producing electric fields inside the head during the CPR, by placing at least two current-carrying electrodes on the head, and applying at least two different electric potentials to the current-carrying electrodes;
    c) measuring at least changes in the electric fields and the currents during the CPR;
    d) estimating changes in the blood volume of the head during the CPR, using a controller to analyze data of the measurements of the electric fields and the currents; and
    e) estimating blood flow in the brain during the CPR, from the changes in blood volume of the head.

* * * * *